United States Patent
Koeda

(10) Patent No.: US 11,128,816 B2
(45) Date of Patent: Sep. 21, 2021

(54) RADIOGRAPHIC IMAGING SYSTEM

(71) Applicant: Konica Minolta, Inc., Tokyo (JP)

(72) Inventor: Keisuke Koeda, Higashimurayama (JP)

(73) Assignee: KONICA MINOLTA, INC., Tokyo (JP)

( * ) Notice: Subject to any disclaimer, the term of this patent is extended or adjusted under 35 U.S.C. 154(b) by 27 days.

(21) Appl. No.: 16/530,309

(22) Filed: Aug. 2, 2019

(65) Prior Publication Data

US 2020/0077036 A1  Mar. 5, 2020

(30) Foreign Application Priority Data

Aug. 31, 2018 (JP) ................................. 2018-162273

(51) Int. Cl.
*H04N 5/32* (2006.01)
*A61B 6/00* (2006.01)
*G01T 1/20* (2006.01)

(52) U.S. Cl.
CPC ......... *H04N 5/3205* (2013.01); *A61B 6/5205* (2013.01); *A61B 6/542* (2013.01); *A61B 6/4283* (2013.01); *G01T 1/20* (2013.01)

(58) Field of Classification Search
CPC ........ H04N 5/32; H04N 5/3205; H04N 5/347; H04N 5/361; H04N 5/3651; A61B 6/4283; A61B 6/5205; A61B 6/542; G01T 1/20; G01T 1/247; G06T 11/005; G06T 11/008
See application file for complete search history.

(56) References Cited

U.S. PATENT DOCUMENTS

| | | | | |
|---|---|---|---|---|
| 6,115,451 A | * | 9/2000 | Boudry | G01T 1/17 250/208.1 |
| 6,393,097 B1 | * | 5/2002 | Aufrichtig | G01T 1/1644 250/370.09 |
| 2006/0291624 A1 | * | 12/2006 | Xue | G03B 42/023 378/98 |
| 2007/0001117 A1 | * | 1/2007 | Sagatelyan | G01N 21/6456 250/341.5 |

(Continued)

FOREIGN PATENT DOCUMENTS

JP 2004516874 A 6/2004
WO 02/052504 A2 7/2002

*Primary Examiner* — Dani Fox
*Assistant Examiner* — Soorena Kefayati
(74) *Attorney, Agent, or Firm* — Lucas & Mercanti, LLP

(57) ABSTRACT

Disclosed is a radiographic imaging system including: radiation detecting elements that is two-dimensionally arrayed; and an image acquiring circuit that acquires an image by causing the radiation detecting elements to accumulate and release charges and reading the released charges, wherein the radiographic imaging system comprises a hardware processor that: controls the image acquiring circuit to successively acquire radiographs while changing at least a binning number; controls the image acquiring circuit to acquire offset images respectively for the radiographs in which a binning number in resetting the radiation detecting elements before acquiring the offset images and binning numbers in acquiring the offset images are equal respectively to a binning number in resetting the radiation detecting elements before acquiring the radiographs and binning numbers in acquiring the radiographs; and performs an offset correction on the radiographs by using the offset images respectively for the radiographs.

5 Claims, 10 Drawing Sheets

(56) References Cited

U.S. PATENT DOCUMENTS

| Publication No. | Date | Inventor | Classification | Subclass |
|---|---|---|---|---|
| 2009/0121143 A1* | 5/2009 | Takenaka | H04N 5/365 | 250/369 |
| 2009/0147921 A1* | 6/2009 | Okamura | A61B 6/5235 | 378/98.12 |
| 2010/0328485 A1* | 12/2010 | Imamura | H04N 5/347 | 348/222.1 |
| 2011/0073769 A1* | 3/2011 | Enomoto | A61B 6/00 | 250/370.08 |
| 2012/0087471 A1* | 4/2012 | Naito | H04N 5/341 | 378/62 |
| 2012/0138808 A1* | 6/2012 | Jung | H04N 5/378 | 250/370.09 |
| 2012/0288062 A1* | 11/2012 | Takasaki | A61B 6/5205 | 378/62 |
| 2013/0021497 A1* | 1/2013 | Kawamura | H04N 5/361 | 348/231.3 |
| 2013/0051519 A1* | 2/2013 | Yang | G06T 11/005 | 378/19 |
| 2014/0029721 A1* | 1/2014 | Niwa | G01T 1/24 | 378/62 |
| 2014/0218567 A1* | 8/2014 | Han | H04N 5/2353 | 348/239 |
| 2014/0232841 A1* | 8/2014 | Ohta | H05G 1/60 | 348/65 |
| 2014/0252243 A1* | 9/2014 | Ohguri | H04N 5/361 | 250/394 |
| 2014/0267837 A1* | 9/2014 | Tsuji | G06T 5/50 | 348/241 |
| 2014/0291541 A1* | 10/2014 | Watanabe | H04N 5/32 | 250/394 |
| 2015/0070529 A1* | 3/2015 | Tanaka | H04N 5/361 | 348/231.6 |
| 2015/0071414 A1* | 3/2015 | Oda | A61B 6/4233 | 378/207 |
| 2015/0189194 A1* | 7/2015 | Tajima | A61B 6/488 | 378/62 |
| 2015/0348290 A1* | 12/2015 | Yi | A61B 6/5205 | 378/98 |
| 2016/0358330 A1* | 12/2016 | Asai | A61B 6/4225 | |
| 2016/0366351 A1* | 12/2016 | Ryu | H04N 5/374 | |
| 2017/0238896 A1* | 8/2017 | Iwai | A61B 6/4241 | |
| 2018/0153496 A1* | 6/2018 | Sasaki | A61B 6/5241 | |

* cited by examiner

FIRST IMAGE  SECOND IMAGE  FIRST OFFSET IMAGE

FIRST IMAGE  FIRST OFFSET IMAGE  IMAGE AFTER CORRECTION

RADIOGRAPHIC IMAGING SYSTEM

BACKGROUND

1. Technological Field

The present invention relates to a radiographic imaging system.

2. Description of the Related Art

There have been developed various radiographic imaging apparatuses with a radiation detector (FPD: Flat Panel Detector) which generates charges by radiation detecting elements according to the dose of an emitted radiation reads the generated charges as image data.

In such a radiographic imaging apparatus, even in a state where radiation irradiation is not performed, a dark charge is generated in each radiation detecting element, due to thermal excitation caused by the heat of the radiation detecting element, and the like, and the charge accumulated in the radiation detecting element includes an offset quantity due to the dark charge. Therefore, for acquiring a high-quality radiograph, typically, a offset image acquiring process of reading the data (hereinafter, referred to as "offset image") of the offset quantity due to the dark charge, from each radiation detecting element, with no radiation irradiation is performed before or after a radiograph acquiring process of acquiring the radiograph by accumulating the charge generated by radiation irradiation in each radiation detecting element and reading the accumulated charge. Then, an offset correction of removing the offset quantity due to the dark charge from the radiograph is performed by subtracting the offset image from the radiograph acquired by the radiograph acquiring process.

In the meantime, in the case of performing an energy subtraction process of continuously irradiating a subject with radiation different in energy distribution and acquiring a plurality of radiographs using the above-described radiographic imaging apparatus, it is necessary to acquire offset images corresponding to the radiographs, respectively.

For example, Patent Literature 1 (JP 2004-516874A) describes: acquiring a first irradiation reading value by irradiating a radiation detector at a first X-ray energy level for a time t1 and performing the reading of the radiation detector; acquiring a second irradiation reading value by irradiating the radiation detector at a second X-ray energy level for a time t2 and performing the reading of the radiation detector; after reset, performing the reading of the radiation detector for obtaining a first offset reading value corresponding to the first irradiation reading value after a time equal to t1; and performing the reading of the radiation detector for obtaining a second offset reading value corresponding to the second irradiation reading value after a time equal to t2.

For acquiring a high-definition image while suppressing an image capacity and a processing time in the energy subtraction process, in the radiographic imaging apparatus, the reading of the charge accumulated in the photographing in which the subject is irradiated with a radiation at a low tube voltage can be performed at a greater binning number than that in the reading of the charge accumulated in the photographing in which the subject is irradiated with a radiation at a high tube voltage.

However, in the technology described in Patent Literature 1, the acquisition of offset images in the case of continuously acquiring a plurality of radiographs while varying the binning number is not considered, and there is a possibility that an artifact is generated in the radiograph after an offset correction.

SUMMARY

The present invention has an object to suppress the generation of the artifact due to the offset correction in the case of acquiring a plurality of radiographs while varying the binning number.

For realizing the above-described object, a radiographic imaging system reflecting an aspect of the present invention includes:

a plurality of radiation detecting elements that is two-dimensionally arrayed; and an image acquiring circuit that acquires an image by causing the radiation detecting elements to accumulate and release charges and reading the released charges, wherein the radiographic imaging system comprises a hardware processor that performs:

a radiograph acquiring process of controlling the image acquiring circuit to successively acquire a plurality of radiographs while changing at least a binning number;

an offset image acquiring process of controlling the image acquiring circuit to acquire a plurality of offset images respectively for the plurality of radiographs in which a binning number in resetting the radiation detecting elements before acquiring the plurality of offset images and binning numbers in acquiring the plurality of offset images are equal respectively to a binning number in resetting the radiation detecting elements before acquiring the plurality of radiographs and binning numbers in acquiring the plurality of radiographs; and an offset correction process of performing an offset correction on the plurality of radiographs by using the plurality of offset images respectively for the plurality of radiographs.

BRIEF DESCRIPTION OF THE DRAWINGS

The objects, advantages and features of the above present invention will become more fully understood from the detailed description given hereinbelow and the appended drawings, and they are not intended to limit the present invention, wherein.

DETAILED DESCRIPTION OF EMBODIMENTS

Hereinafter, one or more embodiments of the present invention will be described with reference to the drawings. However, the scope of the invention is not limited to the disclosed embodiments.

Hereinafter, embodiments of a radiographic imaging system and a radiographic imaging apparatus according to the present invention will be described with reference to the drawings.

Hereinafter, descriptions will be made for the case where a radiographic imaging apparatus is a so-called indirect radiographic imaging apparatus that includes a scintillator and acquires an electric signal by converting an emitted radiation into an electromagnetic wave with a different wavelength such as a visible light. However, the present invention can be applied also to a direct radiographic imaging apparatus. Further, descriptions will be made for the case of a portable radiographic imaging apparatus. However, the present invention can be applied also to a radiographic imaging apparatus that is formed integrally with a support and the like.

[Radiographic Imaging System]

Figure 1:
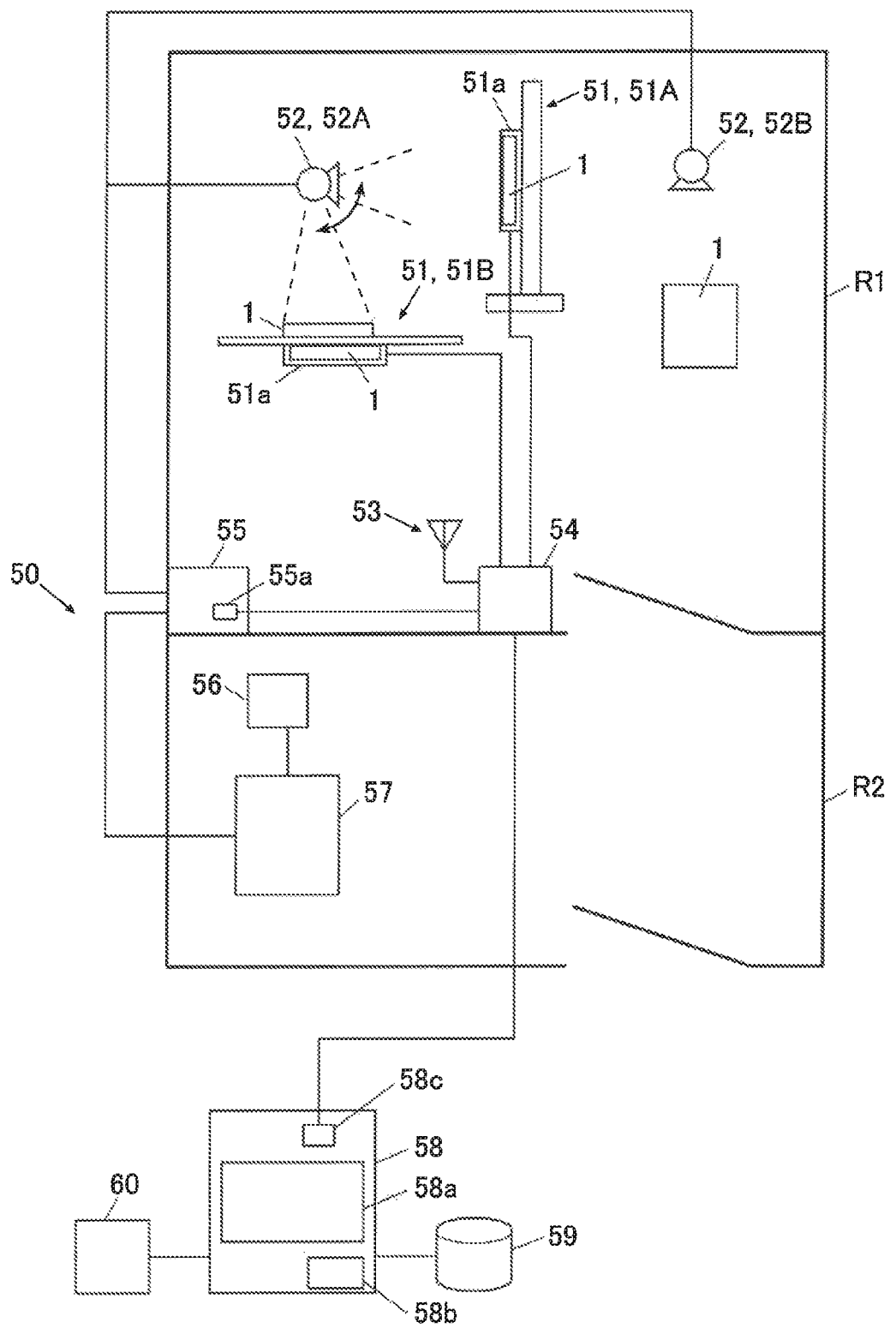
FIG. 1 is a diagram showing the overall configuration of a radiographic imaging system according to an embodiment.

FIG. 1 is a diagram showing the overall configuration of a radiographic imaging system 50 according to an embodiment.

For example, as shown in FIG. 1, the radiographic imaging system 50 is provided with a photographing room R1 where a subject that is a part of the body of an unillustrated patient (a photographing object site of the patient) is irradiated with a radiation and is photographed, a front room R2 that is adjacent to the photographing room R1 and where an operator (user) such as a radiographer performs various operations such as a control for the start of the irradiation of the subject with the radiation, and an area outside them.

Specifically, as shown in FIG. 1, the radiographic imaging system 50 is configured to include a radiographic imaging apparatus 1 that performs a radiograph acquiring process, a console 58 that performs an image process and the like to the image data of the radiograph acquired by the radiographic imaging apparatus 1, a radiation generating apparatus 55 that irradiates the radiographic imaging apparatus 1 with a radiation, and the like.

For example, the photographing room R1 includes a bucky apparatus 51 that allows the radiographic imaging apparatus 1 to be loaded, a radiation irradiating apparatus including a radiation source 52 that includes an X-ray tube (not illustrated) to generate the radiation with which the subject is irradiated and the radiation generating apparatus 55 that controls the radiation source 52, and a radio antenna 53, and there is provided a repeater 54 that relays the communication between the radiographic imaging apparatus 1 and another apparatus such as the console 58 and the radiation generating apparatus 55.

FIG. 1 shows a case where the portable radiographic imaging apparatus 1 is used while being loaded into a cassette holder 51a of the bucky apparatus 51, a case where the radiographic imaging apparatus 1 is used alone without being loaded into the bucky apparatus 51, specifically, a case where the radiographic imaging apparatus 1 is disposed on the upper surface side of a bucky apparatus 51B for recumbent position photographing and the hand or the like of the patient that is the subject is placed on a radiation incidence surface R (see FIG. 2) thereof, and the like. However, the radiographic imaging apparatus 1 may be formed integrally with the bucky apparatus 51, the support and the like.

Here, when the portable radiographic imaging apparatus 1 is used alone without being loaded into the bucky apparatus 51, in addition to the case where the radiographic imaging apparatus 1 is disposed on the upper surface side of the bucky apparatus 51B for recumbent position photographing and the hand or the like of the patient that is the subject is placed on the radiation incidence surface R (see FIG. 2), for example, the radiographic imaging apparatus 1 may disposed on the upper surface side of a bed or the like provided in the photographing room R1 and the hand or the like of the patient that is the subject may be placed on the radiation incidence surface R (see FIG. 2), or for example, the radiographic imaging apparatus 1 may be used while being inserted between the waist, leg or the like of the recumbent patient on the bed and the bed.

The repeater 54 is connected by wire with the console 58 and the radiation generating apparatus 55 through a LAN (Local Area Network) cable or the like. The repeater 54 incorporates a converter (not illustrated) that converts a LAN communication signal or the like for sending information with the radiographic imaging apparatus 1, the console 58 or the like, into a signal for sending information to the radiation generating apparatus 55, and that performs the inverse conversion.

The repeater 54 is connected by wire with the bucky apparatus 51, and the communication between the radiographic imaging apparatus 1 loaded into the bucky apparatus 51 and another apparatus such as the console 58 and the radiation generating apparatus 55 can be performed through the repeater 54 in a wired system.

FIG. 1 shows a configuration in which the radiographic imaging apparatus 1, specifically, the radiographic imaging apparatus 1 not loaded into the bucky apparatus 51 is wirelessly connected with the repeater 54 and the communication between the radiographic imaging apparatus 1 and another apparatus such as the console 58, the radiation generating apparatus 55 can be performed through the repeater 54 in a wireless system. However, the radiographic imaging apparatus 1 and the repeater 54 can be connected by wire and the communication between the radiographic imaging apparatus 1 and another apparatus can be performed through the repeater 54 in a wired system.

The radiographic imaging apparatus 1 may be configured to be capable of being wirelessly connected with the repeater 54 even in a state where the radiographic imaging apparatus 1 is loaded into the bucky apparatus 51.

FIG. 1 shows a case where one bucky apparatus 51A for stereography and one bucky apparatus 51B for recumbent position photographing are provided as the bucky apparatus 51 in the photographing room R1. However, the number and type of the bucky apparatus 51 to be provided in the photographing room R1 are not particularly limited.

Further, FIG. 1 shows a case where one radiation source 52A for the bucky apparatus 51 and one portable radiation source 52B are provided as the radiation source 52 in the photographing room R1. However, the number and type of the radiation source 52 to be provided in the photographing room R1 are not particularly limited.

[Radiation Generating Apparatus]

In the photographing room R1, there is provided the radiation generating apparatus 55 that controls the irradiation of the radiographic imaging apparatus 1 with the radiation from the radiation source 52.

In the embodiment, in the front room R2 adjacent to the photographing room R1, there is provided an operation station 57 for the radiation generating apparatus 55, and on the operation station 57, there is provided an exposure switch 56 that is operated when the user such as a radiographer gives instructions of the start of the radiation irradiation and the like, to the radiation generating apparatus 55.

The exposure switch 56 is a configured by a two-step switch having a first switch and a second switch.

The exposure switch 56 is configured to send a start-up signal to the radiation generating apparatus 55 through the operation station 57 when the first switch is depressed.

The radiation generating apparatus 55 is configured to put the radiation source 52 into a standby state by the start of the rotation of an anode of the X-ray tube of the radiation source 52 and the like, when the radiation generating apparatus 55 receives the start-up signal. Further, the radiation generating apparatus 55 is configured to send a depression notice signal for the first switch to the radiographic imaging apparatus 1 through the repeater 54.

Furthermore, the exposure switch 56 is configured to send a radiation irradiation start signal to the radiation generating apparatus 55 through the operation station 57 when the second switch is depressed.

The radiation generating apparatus 55 is configured to send a depression notice signal for the second switch to the radiographic imaging apparatus 1 through the repeater 54, when the radiation generating apparatus 55 receives the radiation irradiation start signal from the exposure switch 56. When the depression notice signal for the second switch is received and preparations such as the completion of a later-described offset image acquiring process are finished, the radiographic imaging apparatus 1 sends an interlock unlock signal to the radiation generating apparatus 55 through the repeater 54. The radiation generating apparatus 55 is configured to emit the radiation from the X-ray tube of the radiation source 52, when the radiation generating apparatus 55 receives the interlock unlock signal sent from the radiographic imaging apparatus 1 through the repeater 54.

In response to the receiving of the radiation irradiation start signal from the exposure switch 56 and the interlock unlock signal from the radiographic imaging apparatus 1, the radiation generating apparatus 55 can perform the irradiation with the radiation from the radiation source 52 at different tube voltages multiple times. In the embodiment, in the case where a DES (Dual Energy Subtraction) mode (which will be described later in detail) is set as a photographing mode, the radiation generating apparatus 55 performs the irradiation with the radiation from the radiation source 52 at different tube voltages multiple times, in response to the receiving of the radiation irradiation start signal from the exposure switch 56 and the interlock unlock signal from the radiographic imaging apparatus 1.

The radiation generating apparatus 55 is configured to allow the user to perform, for example through the operation of the operation station 57, various controls to the radiation source 52, for example, to allow the user to adjust the position of the radiation source 52 and the radiation irradiation direction such that the radiographic imaging apparatus 1 is appropriately irradiated with the radiation, adjust a diaphragm of the radiation source 52 such that a predetermined region of the radiographic imaging apparatus 1 is irradiated with the radiation, or adjust the radiation source 52 such that the irradiation is performed with an appropriate dose of radiation. The radiation generating apparatus 55 may be configured such that the user manually performs these processes.

[Console]

For example, as shown in FIG. 1, the console 58 is a computer configured to include a display device 58a constituted by a CRT (Cathode Ray Tube), a LCD (Liquid Crystal Display) and the like, a storage 59 constituted by a HDD (Hard Disk Drive) and the like, a controller 58b that controls the operation of each device of the console 58, and the like, a communicator 58c that is connected with the repeater 54 through the LAN cable or the like and that performs the communication with another apparatus such as the radiographic imaging apparatus 1, and an input device 60 constituted by a keyboard, a mouse or the like.

FIG. 1 shows a case where the console 58 is provided outside the photographing room R1 and the front room R2. However, the console 58 may be provided in the front room R2, for example.

FIG. 1 shows a case where the storage 59 is connected with the console 58. However, the storage 59 may be incorporated in the console 58.

When the communicator 58c receives the image data of the radiograph photographed by the radiographic imaging apparatus 1 from the radiographic imaging apparatus 1 through the repeater 54, the controller 58b of the console 58 performs, to the image data, predetermined image processes such as an extension process and an automatic gradation process, and creates a radiograph for diagnosis.

Then, in accordance with an instruction from the input device 60 or the like operated by the user, the controller 58b of the console 58 displays the radiograph for diagnosis, on the display device 58a, or outputs the image data of the radiograph for diagnosis from the communicator 58c or the like and sends the image data of the radiograph for diagnosis to another apparatus (not illustrated) such as an imager or a data management server.

In the embodiment, descriptions will be made for the case where the radiographic imaging apparatus 1 performs correction processes such as the offset correction process and the gain correction process. However, the communicator 39 may send the radiograph and the offset image acquired by the radiographic imaging apparatus 1, to the console 58, and the console 58 may perform the correction processes such as the offset correction process and the gain correction process.

[Radiographic Imaging Apparatus]

Figure 2:
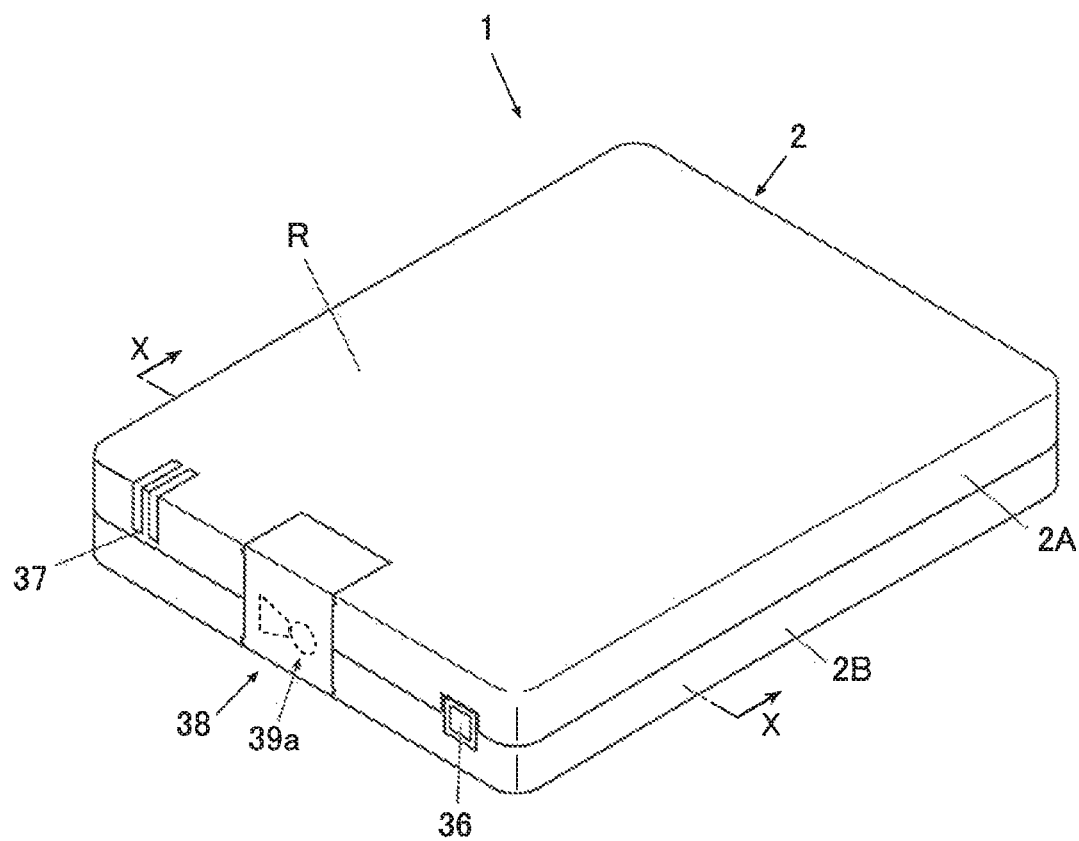
FIG. 2 is a perspective view showing a radiographic imaging apparatus according to the embodiment.
Figure 3:
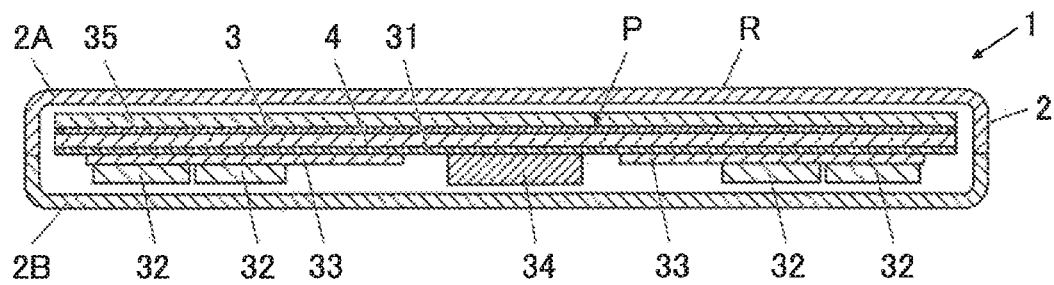
FIG. 3 is a cross-section view taken along line X-X in FIG. 2.

FIG. 2 is an external perspective view of the radiographic imaging apparatus according to the embodiment, and FIG. 3 is a cross-sectional view taken along line X-X in FIG. 2.

As shown in FIG. 2 and FIG. 3, the radiographic imaging apparatus 1 according to the embodiment is configured as a portable (cassette type) apparatus in which a scintillator 3, a substrate 4 and the like are contained within a housing 2.

In the housing 2, at least a surface R (referred to as a "radiation incidence surface R") that is irradiated with the radiation is formed of a material such as a carbon plate or a plastic that transmits the radiation.

FIG. 2 and FIG. 3 show a case where the housing 2 is a so-called lunchbox type formed by a frame plate 2A and a back plate 2B. However, the housing 2 may be a so-called monocoque type integrally formed in a square tube shape.

As shown in FIG. 2, in the embodiment, a power supply switch 36, an indicator 37 constituted by an LED or the like, a lid member 38 configured to be capable of being opened and closed for the replacement of a battery 41 (see FIG. 6 described later), and the like are disposed on a side portion of the housing 2. Further, in the embodiment, an antenna 39a is buried in the side portion of the lid member 38.

In the interior of the housing 2, as shown in FIG. 3, a base 31 is disposed on the lower side of the substrate 4, with an unillustrated lead thin plate composed or the like therebetween, and a PCB substrate 33 provided with electronic components 32 and others, a buffer member 34 and the like are attached to the base 31. In the embodiment, a glass substrate 35 for protecting the substrate 4 and the scintillator 3 is provided on the side of the radiation incidence surface R of the substrate 4 and the scintillator 3.

The scintillator 3 is disposed so as to face a later-described detection part P of the substrate 4. As the scintillator 3, for example, there is used a scintillator that is principally composed of a fluorescent material and that, when receiving the radiation, converts the radiation into electromagnetic waves with wavelengths of 300 to 800 nm, that is, electromagnetic waves mainly including visible lights, to output the electromagnetic waves.

Figure 4:
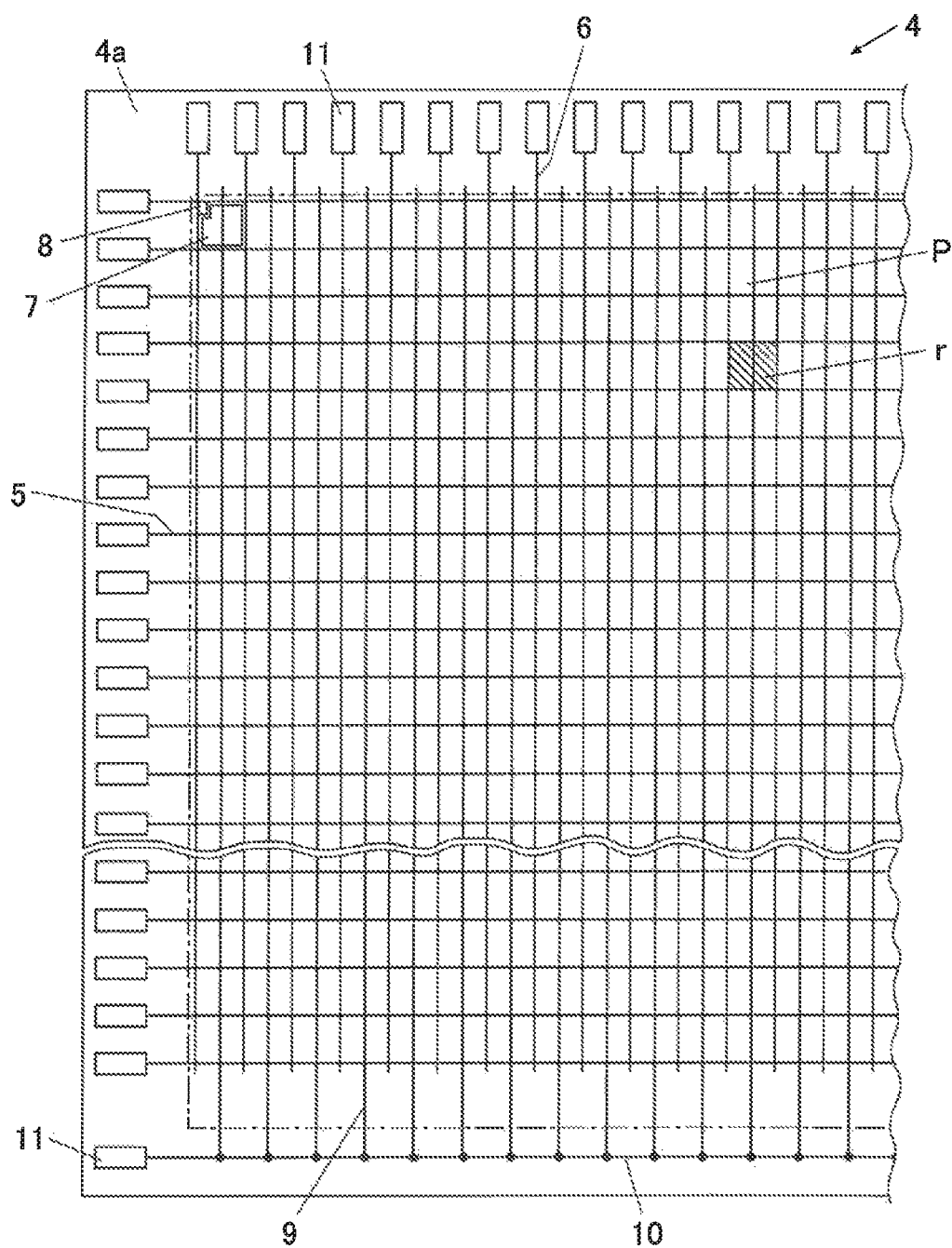
FIG. 4 is a plan view showing the configuration of a substrate of the radiographic imaging apparatus.

In the embodiment, the substrate 4 is composed of a glass substrate, and as shown in FIG. 4, a plurality of scan lines 5 and a plurality of signal lines 6 are arranged so as to intersect each other, on a surface 4a that faces the scintillator 3 of the substrate 4. Radiation detecting elements 7 are respectively provided in regions r separated by the plurality of scan lines 5 and the plurality of signal lines 6 on the surface 4a of the substrate 4.

Thus, the detection part P is the whole of regions r where the plurality of radiation detecting elements 7 two-dimensionally arrayed in the regions r separated by the scan lines 5 and the signal lines 6 are provided, that is, the region indicated by the chain line in FIG. 4.

In the embodiment, as the radiation detecting element 7, a photodiode is used. However, other than the photodiode, for example, a phototransistor or the like can be used.

Figure 5:
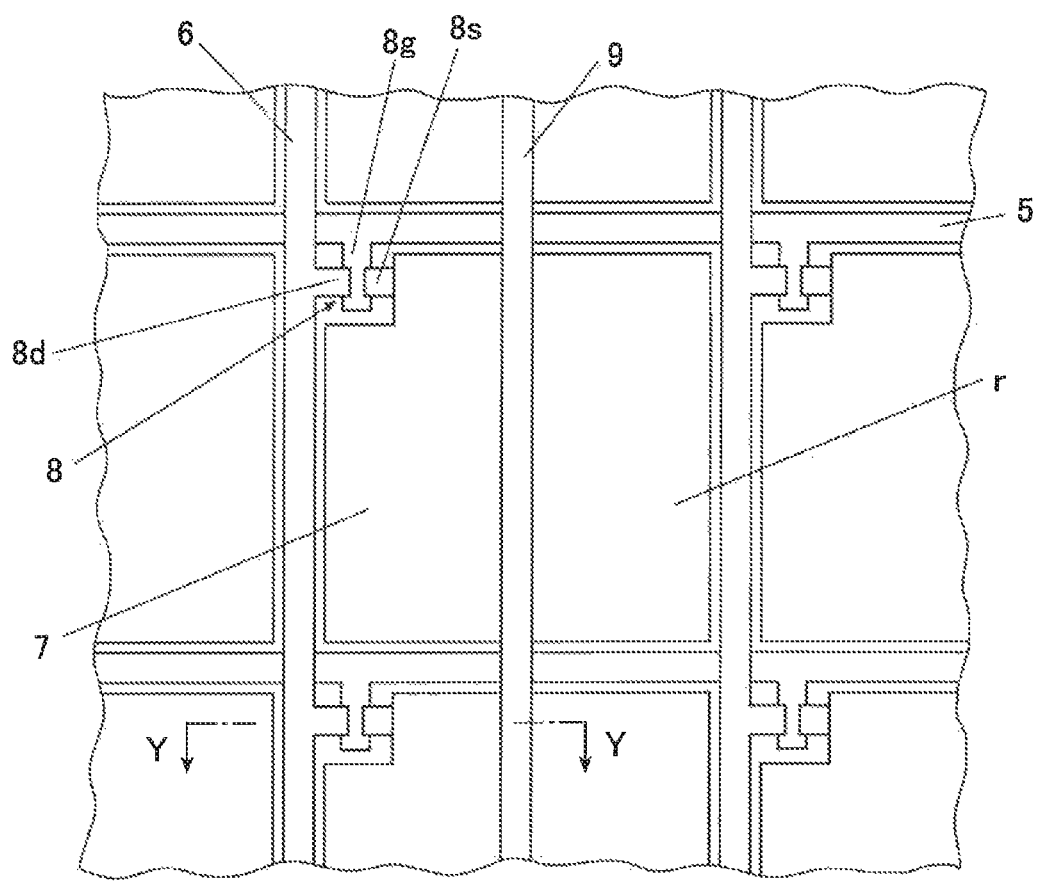
FIG. 5 is an enlarged view showing the configuration of a radiation detecting element, a TFT and the like that are formed in a small region on the substrate in FIG. 4.

As shown in FIG. 4 and FIG. 5, which is an enlarged view of FIG. 4, each radiation detecting element 7 is connected with a source electrode 8s of a TFT 8 that is a switch device. Further, a drain electrode 8d of the TFT 8 is connected with the signal line 6.

When an on-voltage is applied to the scan line 5 connected with the TFT 8 by a later-described scan driver 15 and the on-voltage is applied to a gate electrode 8g through the scan line 5, the TFT 8 is put into an on-state, so that the charge accumulated in the radiation detecting element 7 is released from the radiation detecting element 7 to the signal line 6.

When an off-voltage is applied to the scan line 5 connected with the TFT 8 and the off-voltage is applied to the gate electrode 8g through the scan line 5, the TFT 8 is put into an off-state, so that the release of the charge from the radiation detecting element 7 to the signal line 6 is stopped and the charge generated in the radiation detecting element 7 is held and accumulated in the radiation detecting element 7.

Figure 6:
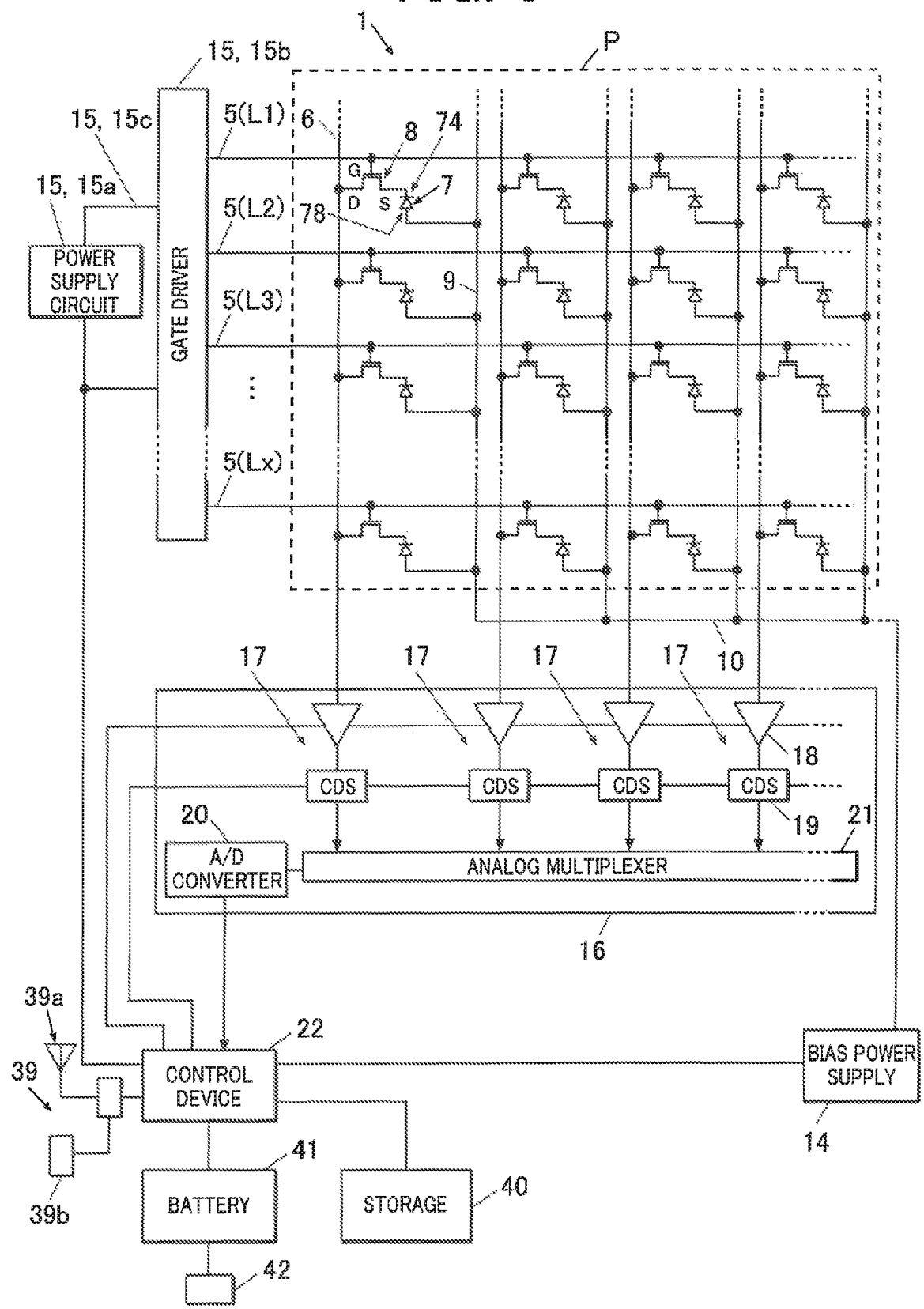
FIG. 6 is a block diagram illustrating an equivalent circuit of a radiographic imaging apparatus.
Figure 7:
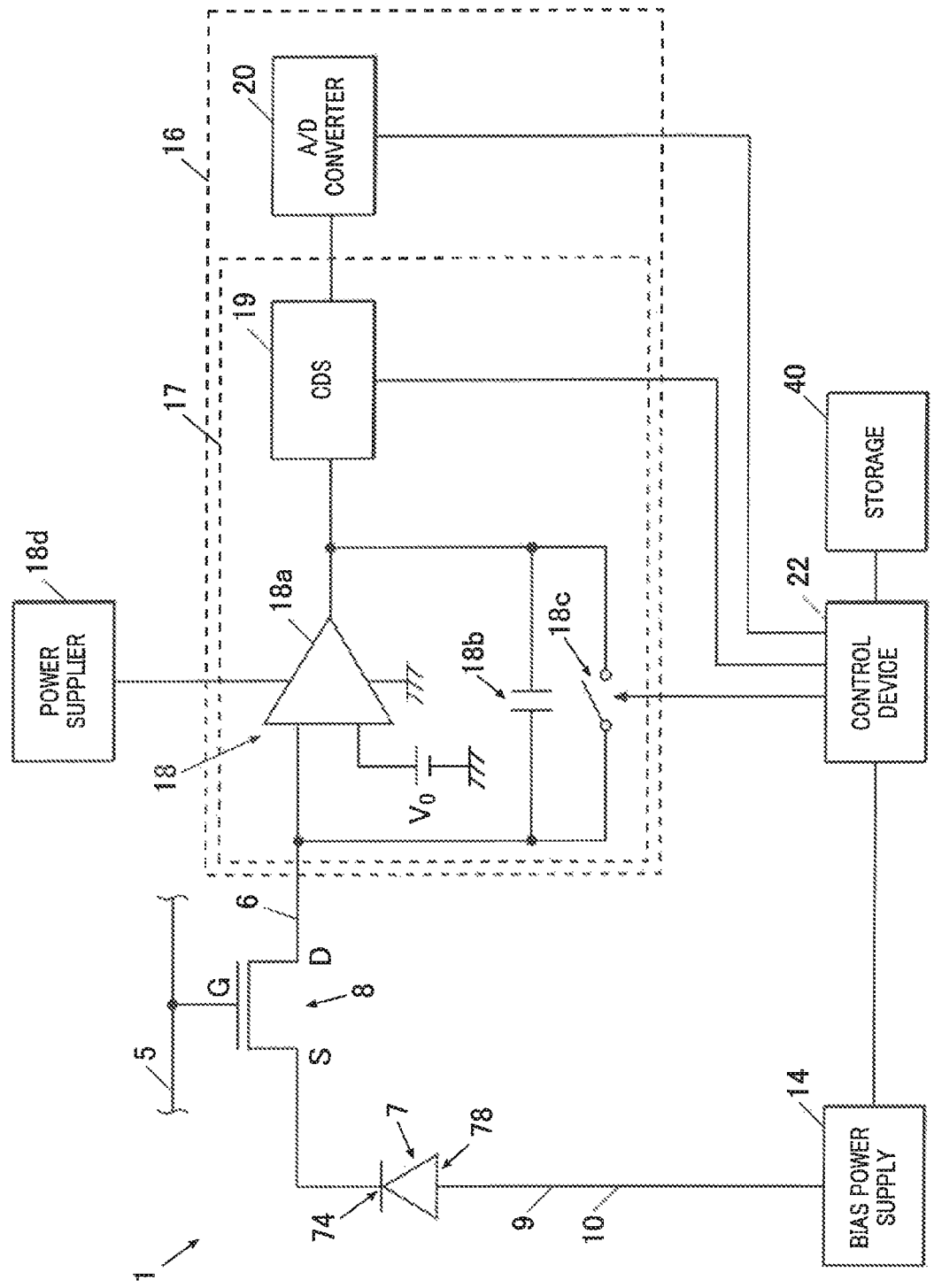
FIG. 7 is a block diagram illustrating an equivalent circuit corresponding to one of pixels that constitute a detection part.

Here, the circuit configuration of the radiographic imaging apparatus 1 will be described. FIG. 6 is a block diagram illustrating an equivalent circuit of the radiographic imaging apparatus 1 according to the embodiment, and FIG. 7 is a block diagram illustrating an equivalent circuit corresponding to one of pixels that constitute the detection part P.

Bias wires 9 are respectively connected with second electrodes 78 of the radiation detecting elements 7 of the detection part P of the substrate 4, and the bias wires 9 are bound by a connecting wire 10 and are connected with a bias power supply 14. The bias power supply 14 applies a bias voltage to the second electrodes 78 of the radiation detecting elements 7 through the connecting wire 10 and the bias wires 9, respectively.

The bias power supply 14 is connected with a later-described control device 22, and the bias voltage to be applied from the bias power supply 14 to the radiation detecting elements 7 is controlled by the control device 22.

In the embodiment, as the bias voltage, a voltage equal to or lower than a voltage to be applied to a first electrode 74 side of the radiation detecting element 7 (that is, a so-called reverse bias voltage) is applied from the bias power supply 14 to the second electrode 78 of the radiation detecting element 7 through the bias wire 9.

The first electrodes 74 of the radiation detecting elements 7 are connected with the source electrodes 8s (which are denoted by S in FIG. 6 and FIG. 7) of the TFTs 8, and the gate electrodes 8g (which are denoted by G in FIG. 6 and FIG. 7) of the TFTs 8 are respectively connected with lines L1 to Lx of the scan lines 5 that extend from the gate driver 15b of the scan driver 15 described later. The drain electrodes 8d (which are denoted by D in FIG. 6 and FIG. 7) of the TFTs 8 are respectively connected with the signal lines 6.

The scan driver 15 includes a power supply circuit 15a that supplies the on-voltage and the off-voltage to the gate driver 15b through a wire 15c, and the gate driver 15b that switches the TFTs 8 between the on-state and the off-state by switching the voltage to be applied to the lines L1 to Lx of the scan lines 5 between the on-voltage and the off-voltage.

As shown in FIG. 6 and FIG. 7, the signal lines 6 are respectively connected with reading circuits 17 formed in a reading IC 16. In the embodiment, one reading circuit 17 is provided for each signal line 6, in the reading IC 16.

The reading circuit 17 is constituted by an amplifier circuit 18, a correlated double sampling circuit 19 and the like. In the reading IC 16, an analog multiplexer 21 and an A/D converter 20 are further provided. In FIG. 6 and FIG. 7, the correlated double sampling circuit 19 is denoted by CDS. In FIG. 7, the analog multiplexer 21 is omitted.

In the embodiment, the amplifier circuit 18 is constituted by a charge amplifier circuit, and is configured to include an operational amplifier 18a, and a capacitor 18b and a charge reset switch 18c that are connected in parallel with the operational amplifier 18a. Further, the amplifier circuit 18 is connected with a power supplier 18d for supplying power to the amplifier circuit 18.

The signal line 6 is connected with the inverting input terminal of the input side of the operational amplifier 18a of the amplifier circuit 18, and a reference potential $V_O$ is applied to the non-inverting input terminal on the input side of the amplifier circuit 18. The reference potential $V_O$ is set to an appropriate value, and in the embodiment, for example, 0 [V] is applied.

The charge reset switch 18c of the amplifier circuit 18 is connected with the control device 22, and the on/off is controlled by the control device 22.

When the TFT 8 is put into the on-state while the charge reset switch 18c is in the off-state (that is, the on-voltage is applied to the gate electrode 8g of the TFT 8 through the scan line 5), the accumulated charge from the radiation detecting element 7 through the TFT 8 in the on-state is released to the signal line 6. The charge flows through the signal line 6, and flows into the capacitor 18b of the amplifier circuit 18, to be accumulated.

In the amplifier circuit 18, a voltage value corresponding to the amount of the charge accumulated in the capacitor 18b is output to the output side of the operational amplifier 18a. Thus, the amplifier circuit 18 performs a charge-voltage conversion by outputting the voltage value corresponding to the amount of the charge output from the radiation detecting element 7.

When the amplifier circuit 18 is reset, the charge reset switch 18c is put into the on-state, and the input side and output side of the amplifier circuit 18 are short-circuited, so that the charge accumulated in the capacitor 18b is discharged. Then, the discharged charge passes through the operational amplifier 18a from the output terminal side of the operational amplifier 18a, and flows from the non-inverting input terminal to the earth or flows to the power supplier 18d. Thereby, the amplifier circuit 18 is reset.

The amplifier circuit 18 may be configured to output electric current corresponding to the charge output from the radiation detecting element 7.

The correlated double sampling (CD S) circuit 19 is connected with the output side of the amplifier circuit 18. The correlated double sampling circuit 19 samples and holds the output voltage of the amplifier circuit 18 before the on-voltage is applied to the scan line 5 with which the radiation detecting element 7 as a signal reading object is connected (while the off-voltage is being applied), reads the signal charge of the radiation detecting element 7 by applying the on-voltage to the corresponding scan line 5, and outputs the difference in the output voltage of the amplifier circuit 18 after the off-voltage is applied to the corresponding scan line 5.

The output voltage of the amplifier circuit 18 after the signal charge is read may be also sampled and held, and the difference may be obtained.

In a reading process of image data from each radiation detecting element 7, the control device 22 controls the amplifier circuit 18 and the correlated double sampling circuit 19, such that the amplifier circuit 18 performs the charge-voltage conversion of the charge released from the radiation detecting element 7 and the correlated double sampling circuit 19 samples the voltage value after the charge-voltage conversion and outputs the voltage value to the downstream side as the image data.

The image data of the radiation detecting elements 7 output from the correlated double sampling circuits 19 is sent to the analog multiplexer 21, and is sequentially sent from the analog multiplexer 21 to the A/D converter 20. Then, the image data is sequentially converted into image data having digital values, by the A/D converter 20, and is sequentially output and saved in a storage 40.

Thus, the radiographic imaging apparatus 1 can acquire the image, by accumulating the charge in the radiation detecting element 7, releasing the accumulated charge from the radiation detecting element 7 and reading the charge, with the image acquiring circuit configured to include the scan driver 15 and the reading circuit 17.

As described later, the control device 22 performs a control so as to perform a process of sequentially switching the lines L1 to Lx of the scan lines 5 to which the on-voltage is applied from the gate driver 15b of the scan driver 15, and reading the image data from the respective radiation detecting elements 7 described above for each switching.

The control device 22 is constituted by an unillustrated computer in which a CPU (Central Processing Unit), a ROM (Read Only Memory), a RAM (Random Access Memory), an input-output interface and the like are connected with a bus, an unillustrated FPGA (Field Programmable Gate Array), and the like. The control device 22 may be constituted by a dedicated control circuit. The control device 22 controls the operation and the like of each member of the radiographic imaging apparatus 1.

As shown in FIG. 6 and the like, the control device 22 is connected with the storage 40 constituted by a DRAM (Dynamic RAM) and the like.

In the embodiment, the control device 22 is connected with the communicator 39. The communicator 39 performs the sending and receiving of data and signals for the exterior through the antenna 39a or the connector 39b, in a wireless system or a wired system.

Furthermore, in the embodiment, the control device 22 is connected with the battery 41 for supplying power to function devices such as the detection part P, the scan driver 15, the reading circuit 17, the storage 40 and the bias power supply 14. Further, to the battery 41, a connecting terminal 42 that connects an unillustrated charging apparatus and the battery 41 when power is supplied from the charging apparatus to the battery 41 such that the battery 41 is charged is attached.

The control device 22 controls the operation of each function device of the radiographic imaging apparatus 1, for example, controls the bias power supply 14 to set the bias voltage to be applied from the bias power supply 14 to each radiation detecting element 7, controls the on/off of the charge reset switch 18c of the amplifier circuit 18 of the reading circuit 17, or controls the on/off of the sample and hold function by sending the pulse signal to the correlated double sampling circuit 19.

<Operation of Radiographic Imaging System>

The operation of the radiographic imaging system 50 will be described below.

In the embodiment, descriptions will be made with an example of acquiring a first image by the irradiation with a radiation at a first tube voltage, subsequently acquiring a second image by the irradiation with a radiation at a second tube voltage (first tube voltage<second tube voltage), and acquiring offset images (a first offset image and a second offset image) respectively for the first image and the second image before the acquisition of the first image and the second image in a mode (referred to as a DES mode) in which a difference image is generated using the first image and the second image.

First, a photographing operator performs a preparation for photographing. For example, the photographing operator selects a photographing menu (for example, a photographing mode (the DES mode herein), a photographing site, a photographing direction and the like) through the input device 60 on the console 58, and inputs an instruction for start of photographing. Further, the photographing operator performs the positioning of the subject, the radiation source 52 and the radiographic imaging apparatus 1.

In the console 58, when the photographing menu is selected and the photographing start instruction is input through the input device 60, the controller 58b sends the photographing start instruction with the selected photographing menu, to the radiation generating apparatus 55 and the radiographic imaging apparatus 1, through the communicator 58c. When receiving the photographing menu, the radiation generating apparatus 55 sets a radiation irradiation condition corresponding to the photographing menu (for example, tube currents, tube voltages and irradiation times in a radiation irradiation (first irradiation) for acquiring the first image and a radiation irradiation (second irradiation) for acquiring the second image, a radiation irradiation interval between the first irradiation and the second irradiation, and the like).

When receiving the photographing menu, the control device 22 of the radiographic imaging apparatus 1 reads a radiograph acquisition condition corresponding to the photographing menu (for example, an image acquisition condition (a charge accumulation time (accumulation time) Ti1, a binning number, a reading scan cycle Tr1, and an on-time Ton1 of the TFT 8 in the reading scan cycle) for the first image, an image acquisition condition (an accumulation time Ti2, a binning number, a reading scan cycle Tr2, and an on-time Ton2 of the TFT 8 in the reading scan cycle) for the second image, a reset condition (a binning number, a reset scan cycle, and an on-time of the TFT 8 in the reset scan cycle) for the radiation detecting elements 7 before the image acquisition, and the like), and an offset image acquisition condition (for example, an image acquisition condition (an accumulation time, a binning number, a reading scan cycle, and an on-time of the TFT 8 in the reading scan cycle) for the first offset image, an image acquisition condition (an accumulation time, a binning number, a reading scan cycle, an on-time of the TFT 8 in the reading scan cycle) for the second offset image, a reset condition (a binning number, a reset scan cycle, an on-time of the TFT 8 in the reset scan cycle) for the radiation detecting elements 7 before the image acquisition, and the like), from the storage 40, and sets the radiograph acquisition condition.

Here, the reset means that as an excess charge such as a dark charge accumulated in each radiation detecting element 7 is released before charge is accumulated in each of the radiation detecting element 7 for the image acquisition.

The binning number means the number of pixels that are regarded as one pixel. For example, the binning in the longitudinal direction (the extending direction of the signal line 6; the same applies hereinafter) can be realized by concurrently turning on the gate electrodes 8g of a plurality of adjacent scan lines 5 (analog binning). The binning in the lateral direction (the extending direction of the scan line 5; the same applies hereinafter) can be realized by adding or averaging the values of a plurality of adjacent pixels in the lateral direction of the image data (digital binning). In the embodiment, the binning number in the longitudinal direction at the time of the first image acquisition>the binning number in the longitudinal direction at the time of the second image acquisition is satisfied. By increasing the binning number in the longitudinal direction at the time of the first image acquisition, it is possible to perform a high-speed reading of the first image. Therefore, it is possible to shorten the photographing interval between the first image and the second image, and it is possible to suppress an artifact of the photographed image due to a body motion of the subject.

In the embodiment, descriptions will be made with an example in which the binning number in the longitudinal direction x the binning number in the lateral direction at the time of the first image acquisition is set to 2×1, and the binning number in the longitudinal direction x the binning number in the lateral direction at the time of the second image acquisition and the binning number in the longitudinal direction x the binning number in the lateral direction at the time of the reset before the image acquisition are set to 1×1. In the following description, the binning number is expressed as the binning number in the longitudinal direction x the binning number in the lateral direction. For example, the binning number (2×1) means that the binning number in the longitudinal direction is 2 and the binning number in the lateral direction is 1.

The reading scan cycle means a time in which the charge is read from each radiation detecting element 7 and the image data is acquired, and is nearly equal to the on-time of the TFT 8+the processing time of the correlated double sampling circuit 19. The reset scan cycle means a time in which the charge is released (read) from each radiation detecting element 7, and is nearly equal to the on-time of the TFT 8. The reset scan cycle can be shorten compared to the reading scan cycle, because the processing time of the correlated double sampling circuit 19 is unnecessary. Incidentally, the reading scan can be used instead of the reset scan, and in this case, although the reset scan cycle is equivalent to the reading scan cycle, the design can be simplified because the number of kinds of scan sequences decreases. It is preferable that which advantage has priority depend on the design principle.

In the embodiment, the binning number at the time of the first offset image acquisition is set so as to be equal to the binning number at the time of the first image acquisition, and the binning number at the time of the second offset image acquisition is set so as to be equal to the binning number at the time of the second image acquisition. Further, the binning number at the time of the reset of the radiation detecting elements 7 before a series of acquisitions of the offset images is set so as to be the same as the binning number at the time of the reset of the radiation detecting elements 7 before a series of acquisitions of the radiographs. When the binning number at the time of the reset before the image acquisition or at the time of the image acquisition differs between the time of the radiograph acquisition and the time of the offset image acquisition, the artifact is generated in the radiograph after an offset correction. However, by using the same the binning number between the time of the radiograph acquisition and the time of the offset image acquisition, it is possible to suppress the generation of the artifact.

Further, it is preferable to use the same accumulation time at the time of the first offset image acquisition, as the accumulation time Ti1 at the time of the first image acquisition, and to use the same accumulation time at the time of the second offset image acquisition, as the accumulation time Ti2 at the time of the second image acquisition. By using the same accumulation time at the time of the acquisition of the radiograph as the accumulation time at the time of acquisition of corresponds offset image, it is possible to perform a more accurate offset correction.

Furthermore, it is preferable to use the same reading scan cycle and the on-time of the TFT 8 in the reading scan cycle for the first offset image, as the reading scan cycle Tr1 and the on-time Ton1 of the TFT 8 in the reading scan cycle for the first image, respectively. Further, it is preferable to use the same reading scan cycle and the on-time of the TFT 8 in the reading scan cycle for the second offset image, as the reading scan cycle Tr2 and the on-time Ton2 of the TFT 8 in the reading scan cycle for the second image, respectively. Further, it is preferable to use the same reset scan cycle and the on-time of the TFT 8 in the reset scan cycle at the time of the reset before the offset image acquisition, as the reset scan cycle and the on-time of the TFT 8 in the reset scan cycle at the time of the reset before the radiograph acquisition, respectively. By using the same image acquisition condition for the offset image as the image acquisition condition for the radiograph in this way, it is possible to perform a more accurate offset correction.

In the embodiment, descriptions will be made with an example in which the image acquisition condition for the first offset image is set so as to be equal to the image acquisition condition for the first image, the image acquisition condition for the second offset image is set so as to be equal to the image acquisition condition for the second image, and the reset condition before a series of offset image acquisitions is set so as to be equal to the reset condition before the radiograph acquisition.

In the embodiment, the reading scan at the time of the second offset image acquisition is used instead of the reset scan of the radiation detecting elements 7 before the image acquisition at the time of the radiograph acquisition, and the binning number, the reset scan cycle and the on-time of the TFT 8 in the reset scan cycle at the time of the reset of the radiation detecting elements 7 are set so as to be equal to the binning number (1×1), the reading scan cycle Tr2, the on-time Ton2 of the TFT 8 at the time of the second image acquisition, but the present invention is not limited to this.

The radiation irradiation condition and the image acquisition condition corresponding to the photographing menu may be stored in the storage 59, and the console 58 may read the radiation irradiation condition and the image acquisition condition from the storage 59, and may send the radiation irradiation condition and the image acquisition condition by the communicator 58c through the repeater 54 to the radiation generating apparatus 55 and the radiographic imaging apparatus 1, to set them.

Figure 8:
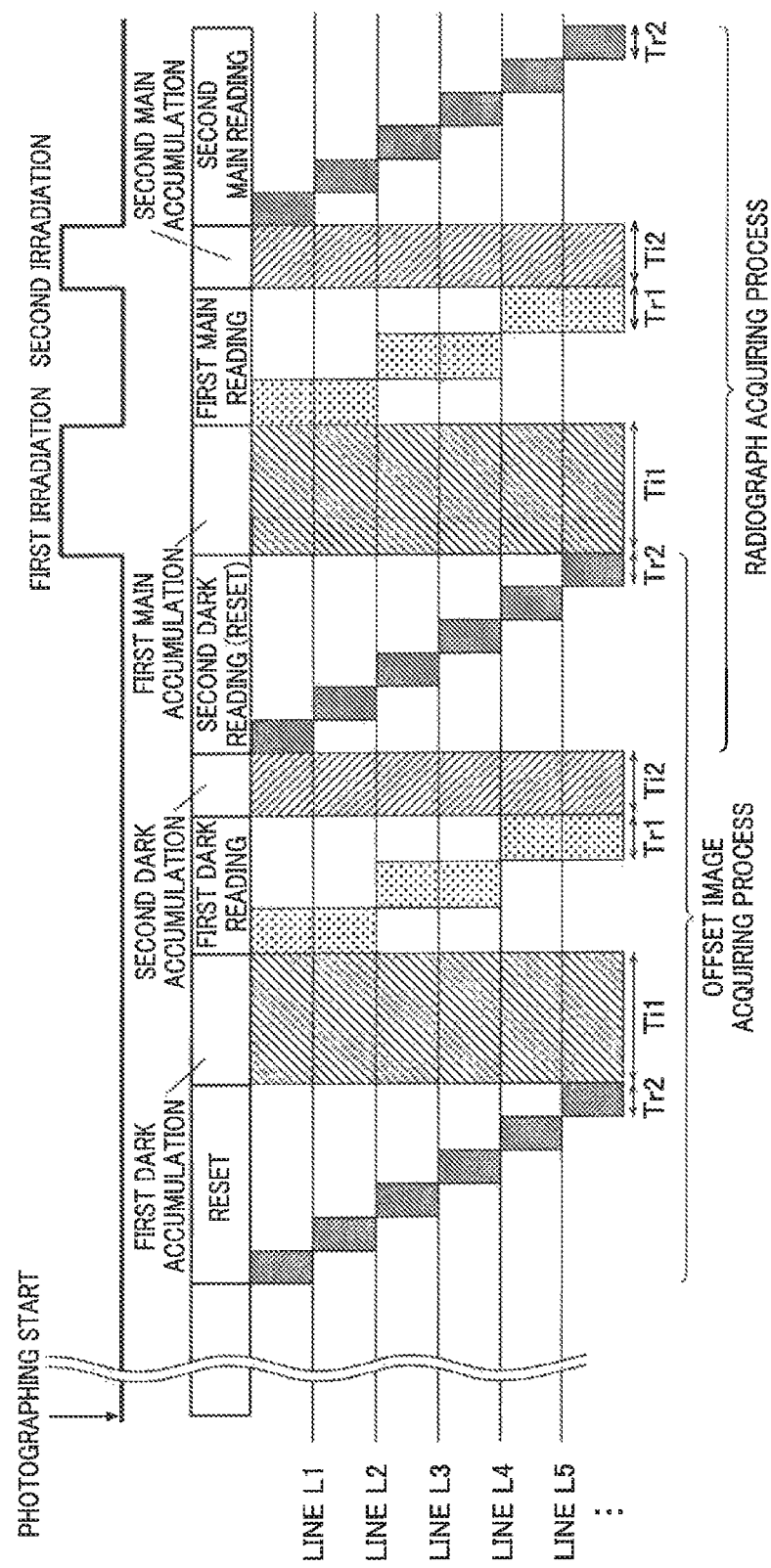
FIG. 8 is a diagram schematically showing an image acquiring sequence in a radiographic imaging apparatus 1 after a photographing start instruction in a first embodiment.

When the setting of the image acquisition condition ends, the control device 22 executes an image acquiring sequence, in the radiographic imaging apparatus 1. FIG. 8 is a diagram schematically showing the image acquiring sequence that is executed in the radiographic imaging apparatus 1 after the photographing start instruction.

As shown in FIG. 8, first, the control device 22 of the radiographic imaging apparatus 1 performs an offset image acquiring process.

In the offset image acquiring process, first, the control device 22 controls the scan driver 15 and the like, to reset each of the radiation detecting elements 7, with the binning number, the reset scan cycle and the on-time of the TFT 8 in the reset scan cycle at the time of the reset of the radiation detecting elements 7 before the image acquisition (that is, the binning number (1×1), the reset scan cycle Tr2 and the on-time Ton2 of the TFT 8 in the reset scan cycle at the time of the reset before the radiograph acquisition), which are previously set.

Next, the control device 22 transitions to a charge accumulation mode of accumulating the charge in the radiation detecting elements 7 by applying the off-voltage to all the scan lines 5 through the scan driver 15, and waits for the previously set accumulation time for the first offset image (that is, the accumulation time Ti1 at the time of the first image acquisition), in a state where the radiographic imaging apparatus 1 is not irradiated with the radiation, to perform the accumulation of the dark charge (first dark accumulation).

Next, the control device 22 transitions to a reading mode, and controls the scan driver 15, the reading circuit 17 and the like, to read the charge accumulated in each radiation detecting element 7, with the binning number, the reading scan cycle and the on-time of the TFT 8 in the reading scan cycle at the time of the first offset image acquisition (that is, the binning number (2×1), the reading scan cycle Tr1 and the on-time Ton1 of the TFT 8 in the reading scan cycle at the time of the first image acquisition), which are previously set, and acquire the image data of the first offset image (first dark reading).

Next, the control device 22 transitions to the charge accumulation mode again. The control device 22 applies the off-voltage to all the scan lines 5 through the scan driver 15, and waits for the previously set accumulation time for the second offset image (that is, the accumulation time Ti2 at the time of the second image acquisition), in a state where the radiographic imaging apparatus 1 is not irradiated with the radiation, to perform the accumulation of the dark charge (second dark accumulation).

Next, the control device 22 transitions to the reading mode, and controls the scan driver 15, the reading circuit 17 and the like, to read the charge accumulated in each radiation detecting element 7, with the binning number, the reading scan cycle and the on-time of the TFT 8 in the reading scan cycle at the time of the second offset image acquisition (that is, the binning number (1×1), the reading scan cycle Tr2 and the on-time Ton2 of the TFT 8 in the reading scan cycle at the time of the second image acquisition), which are previously set, and acquire the image data of the second offset image (second dark reading).

The second dark reading is concurrently the reset of the radiograph acquiring process.

By the above offset image acquiring process, the first offset image and the second offset image are acquired. The control device 22 repeatedly executes the offset image acquiring process until the depression notice signal for the second switch of the exposure switch 56 is received from the radiation generating apparatus 55.

When the preparation for photographing is completed, the photographing operator depresses the first switch of the exposure switch 56, and subsequently depresses the second switch. When the first switch is depressed, the exposure switch 56 sends the start-up signal to the radiation generating apparatus 55 through the operation station 57. When receiving the start-up signal, the radiation generating apparatus 55 puts the radiation source 52 into the standby state, for example, by starting the rotation of the anode of the X-ray tube of the radiation source 52.

When the second switch is depressed, the exposure switch 56 sends the radiation irradiation start signal to the radiation generating apparatus 55 through the operation station 57.

When receiving the radiation irradiation start signal from the exposure switch 56, the radiation generating apparatus 55 sends the depression notice signal for the second switch to the radiographic imaging apparatus 1 through the repeater 54. When the depression notice signal for the second switch is received and preparations such as the completion of the offset image acquiring process in execution are finished, the radiographic imaging apparatus 1 sends the interlock unlock signal to the radiation generating apparatus 55 through the repeater 54. When receiving the interlock unlock signal sent from the radiographic imaging apparatus 1 through the repeater 54, the radiation generating apparatus 55 performs the irradiation with the radiation from the X-ray tube of the radiation source 52, based on the radiation irradiation condition.

When the interlock unlock signal is sent, the control device 22 transitions to the charge accumulation mode. The control device 22 applies the off-voltage to all the scan lines 5 through the scan driver 15, and waits for the previously set accumulation time Ti1 for the first image, to accumulate the charge generated in each radiation detecting element 7 by the irradiation with the radiation, in each of the radiation detecting element 7 (first main accumulation).

Next, the control device 22 transitions to the reading mode, and controls the scan driver 15, the reading circuit 17 and the like, to read the charge accumulated in each radiation detecting element 7, with the binning number (2×1), the reading scan cycle Tr1 and the on-time Ton1 of the TFT 8 in the reading scan cycle at the time of the first image acquisition, which are previously set, and acquire the image data of the first image (first main reading).

Next, the control device 22 transitions to the charge accumulation mode again. The control device 22 applies the off-voltage to all the scan lines 5 through the scan driver 15, and waits for the previously set accumulation time Ti2 for the second image, to accumulate the charge generated in each radiation detecting element 7 by the irradiation with the radiation, in each of the radiation detecting element 7 (second main accumulation).

Next, the control device 22 transitions to the reading mode, and controls the scan driver 15, the reading circuit 17 and the like, to read the charge accumulated in each radiation detecting element 7, with the binning number (1×1), the reading scan cycle Tr2 and the on-time Ton2 of the TFT 8 in the reading scan cycle at the time of the second image acquisition, which are previously set, and acquire the image data of the second image (second main reading).

By the above processes from the reset before the image acquisition (the second dark reading of the last offset image acquiring process) to the second main reading process (radiograph acquiring process), the first image and the second image are acquired. That is, the radiographic imaging apparatus 1 can perform the offset image acquiring process and the radiograph acquiring process by repeating the same drive.

After the radiograph acquiring process, from the signal value of each pixel of the first image, the control device 22 subtracts the signal value of the corresponding pixel of the first offset image, to perform the offset correction process. Further, from the signal value of each pixel of the second image, the control device 22 subtracts the signal value of the corresponding pixel of the second offset image, to perform the offset correction process. Here, in the offset correction process, the first offset image and second offset image acquired in the offset image acquiring process just before the radiograph acquiring process may be used, or average or median of first offset images and second offset images acquired in a plurality of offset image acquiring processes may be calculated and used as the first offset image and the second offset image, respectively. By evaluating the average or median of a plurality of offset images, it is possible to reduce offset noise. In the case where an offset difference is generated due to a difference in the acquisition time of the offset image, both the coincidence of the offset and the reduction in offset noise may be achieved by evaluating the average after giving a heavy weight to an image with a late acquisition time and giving a light weight to an old image.

In addition, the control device 22 performs correction processes such as the gain correction process, a defective pixel correction process and a lag (residual image) correction process, to the first image and the second image, and sends the image data of the corrected first image and second image to the console 58 through the communicator 39.

When receiving the image data of the first image and the second image through the communicator 58c, the controller 58b of the console 58 generates the difference image between the first image and the second image, after equalizing the binning number between the first image and the second image by performing an enlargement interpolation process to the first image or performing a reduction interpolation (digital binning) process to the second image, and stores the first image, the second image and the difference image in the storage 59, in association with patient information, photographing condition and the like, or displays the first image, the second image and the difference image on the display device 58a. The difference image can be generated, for example, by multiplying signal values of mutually corresponding pixels of the first image and the second image by weighting factors and obtaining the difference.

Thus, in the case of continuously photographing a plurality of radiographs (the first image and the second image) different in binning number, the radiographic imaging apparatus 1 acquires a plurality of offset images for the plurality of radiographs in which the binning number in resetting before the image acquisition and the binning numbers in acquiring the offset images are respectively equal to those in resetting and acquiring the plurality of radiographs, and performs the offset correction process to the radiographs, respectively. Accordingly, it is possible to suppress the generation of the artifact in each of the radiographs due to the offset correction.

Furthermore, it is possible to perform a more accurate offset correction, by using the same accumulation time at the time of the acquisition of each of the plurality of offset images as the accumulation time at the time of the photographing of the corresponding radiograph.

Furthermore, it is possible to perform a more accurate offset correction, by acquiring a plurality of offset images respectively for the plurality of radiographs in which at least one of the reset scan cycle, the on-time of the TFT 8 in the reset scan cycle, the reading scan cycle at the time of each image acquisition and the on-time of the TFT 8 in the reading scan cycle is equal to those in acquiring the plurality of radiographs. Furthermore, by acquiring a plurality of offset images respectively for the plurality of radiographs in which all of the reset scan cycle, the on-time of the TFT 8 in the reset scan cycle, the reading scan cycle at the time of each image acquisition and the on-time of the TFT 8 in the reading scan cycle are equal to those in acquiring the plurality of radiographs, it is possible to nearly equalize the effective accumulation time (the total accumulation time from the completion of the last reset to the start of the reading after the accumulation of the charge) for each line of the scan lines 5 at the time of each offset image acquisition, with the effective accumulation time at the time of the corresponding radiograph acquisition, and therefore, it is possible to perform a more accurate offset correction.

Further, in the DES mode, by setting a greater number than 1 as the binning number in the longitudinal direction at the time of the acquisition of the first image that is photographed earlier, it is possible to perform a high-speed reading of the first image. Therefore, it is possible to shorten the photographing interval between the first image and the second image, and it is possible to suppress the artifact in the photographed image due to the body motion of the subject. Further, the first image photographed at a low tube voltage has a low graininess. However, it is possible to reduce the noise of the first image, by performing the reading of the charge accumulated by the photographing in which the subject is irradiated with the radiation at a low tube voltage (that is, the acquisition of the first image) at a greater binning number than that in the reading of the charge accumulated by the photographing in which the subject is irradiated with the radiation at a high tube voltage (that is, the acquisition of the second image).

Second Embodiment

A second embodiment of the present invention will be described below.

In the second embodiment, descriptions will be made with an example of acquiring the offset images (the first offset image and the second offset image) for the first image and the second image after the acquisition of the first image and the second image in the DES mode.

The configuration of the second embodiment is the same as the configuration described in the first embodiment, and therefore, the description is omitted. In the following, the operation of the second embodiment will be described.

First, the photographing operator performs a preparation for photographing. For example, the photographing operator selects a photographing menu (for example, the photographing mode (the DES mode herein), the photographing site, the photographing direction and the like) through the input device 60 on the console 58, and inputs an instruction for start of photographing. Further, the photographing operator performs the positioning of the subject, the radiation source 52 and the radiographic imaging apparatus 1.

In the console 58, when the photographing menu is set and the photographing start instruction is input through the input device 60, the controller 58b sends the photographing start instruction with the selected photographing menu, to the radiation generating apparatus 55 and the radiographic imaging apparatus 1, through the communicator 58c.

When receiving the photographing menu, the radiation generating apparatus 55 sets a radiation irradiation condition corresponding to the photographing menu (for example, tube currents, tube voltages and irradiation times in the radiation irradiation (first irradiation) for acquiring the first image and the radiation irradiation (second irradiation) for acquiring the second image, a radiation irradiation interval between the first irradiation and the second irradiation, and the like).

When receiving the photographing menu, the control device 22 of the radiographic imaging apparatus 1 sets a radiograph acquisition condition and offset image acquisition condition corresponding to the photographing menu. Examples of the radiograph acquisition condition and the offset image acquisition condition are the same as the examples described in the first embodiment, and therefore, the description is omitted.

In the embodiment, descriptions will be described with an example in which the binning number of the first image is set to 2×1, the binning number of the second image is set to 1×1, the binning number in the reset is set to 2×1, the reset scan cycle before the image acquisition is set to Tr0 and the on-time of the TFT 8 in the reset scan cycle is set to Ton0. The other setting of the radiograph acquisition condition and the offset image acquisition condition is the same as the setting described in the first embodiment, and therefore, the description is omitted.

The radiation irradiation condition and image acquisition condition corresponding to the photographing menu may be stored in the storage 59, and the console 58 may read the radiation irradiation condition and the image acquisition condition from the storage 59, and may send the read conditions by the communicator 58c through the repeater 54 to the radiation generating apparatus 55 and the radiographic imaging apparatus 1, to set them.

Figure 9:
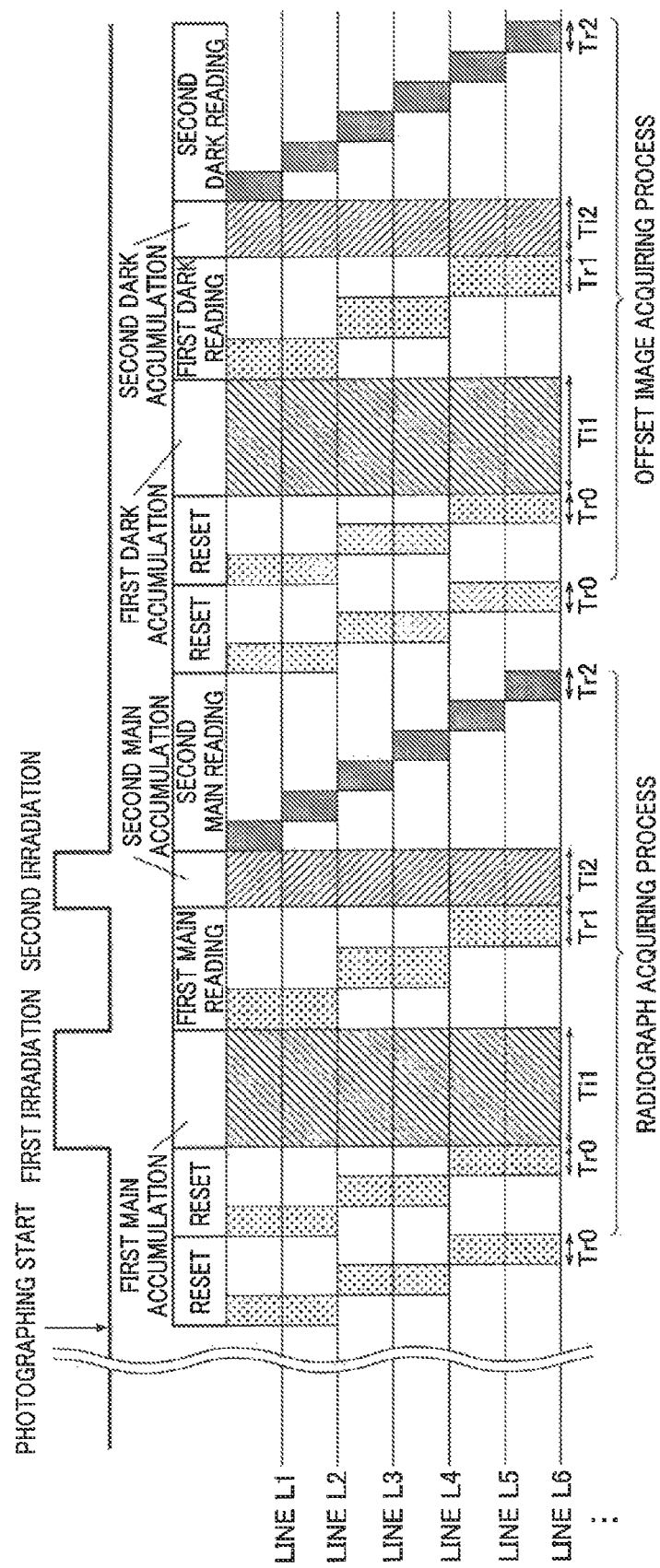
FIG. 9 is a diagram schematically showing an image acquiring sequence in the radiographic imaging apparatus 1 after the photographing start instruction in a second embodiment.

When the setting of the image acquisition condition ends, the control device 22 executes an image acquiring sequence, in the radiographic imaging apparatus 1. FIG. 9 is a diagram schematically showing the image acquiring sequence that is executed in the radiographic imaging apparatus 1 after the photographing start instruction in the second embodiment.

As shown in FIG. 9, first, the control device 22 of the radiographic imaging apparatus 1 controls the scan driver 15 and the like, to reset each of the radiation detecting elements 7, with the binning number (2×1), the reset scan cycle Tr0 and the on-time Ton0 of the TFT 8 in the reset scan cycle at the time of the reset of the radiation detecting elements 7 before the image acquisition, which are previously set. The control device 22 repeatedly executes the reset until the depression notice signal for the second switch of the exposure switch 56 is received from the radiation generating apparatus 55.

When the preparation for photographing is completed, the photographing operator depresses the first switch of the exposure switch 56, and subsequently depresses the second switch. When the first switch is depressed, the exposure switch 56 sends the start-up signal to the radiation generating apparatus 55 through the operation station 57. When receiving the start-up signal, the radiation generating apparatus 55 puts the radiation source 52 into the standby state, for example, by starting the rotation of the anode of the X-ray tube of the radiation source 52.

When the second switch is depressed, the exposure switch 56 sends the radiation irradiation start signal to the radiation generating apparatus 55 through the operation station 57.

When receiving the radiation irradiation start signal from the exposure switch 56, the radiation generating apparatus 55 sends the depression notice signal for the second switch to the radiographic imaging apparatus 1 through the repeater 54. When the depression notice signal for the second switch is received and preparations such as the completion of the reset are finished, the radiographic imaging apparatus 1 sends the interlock unlock signal to the radiation generating apparatus 55 through the repeater 54. When receiving the interlock unlock signal sent from the radiographic imaging apparatus 1 through the repeater 54, the radiation generating apparatus 55 performs the irradiation with the radiation from the X-ray tube of the radiation source 52, based on the radiation irradiation condition.

When the interlock unlock signal is sent, the control device 22 transitions to the charge accumulation mode. The control device 22 applies the off-voltage to all the scan lines 5 through the scan driver 15, and waits for the previously set accumulation time Ti1 for the first image, to accumulate the charge generated in each radiation detecting element 7 by the irradiation with the radiation, in each of the radiation detecting element 7 (first main accumulation).

Next, the control device 22 transitions to the reading mode, and controls the scan driver 15, the reading circuit 17 and the like, to read the charge accumulated in each radiation detecting element 7, with the binning number (2×1), the reading scan cycle Tr1 and the on-time Ton1 of the TFT 8 in the reading scan cycle at the time of the first image acquisition, which are previously set, and acquire the image data of the first image (first main reading).

Next, the control device 22 transitions to the charge accumulation mode again. The control device 22 applies the off-voltage to all the scan lines 5 through the scan driver 15, and waits for the previously set accumulation time Ti2 for the second image, to accumulate the charge generated in each radiation detecting element 7 by the irradiation with the radiation, in each of the radiation detecting element 7 (second main accumulation).

Next, the control device 22 transitions to the reading mode, and controls the scan driver 15, the reading circuit 17 and the like, to read the charge accumulated in each radiation detecting element 7, with the binning number (1×1), the reading scan cycle Tr2 and the on-time Ton2 of the TFT 8 in the reading scan cycle at the time of the second image acquisition, which are previously set, and acquire the image data of the second image (second main reading).

By the above processes from the reset before the image acquisition to the second main reading process (radiograph acquiring process), the first image and the second image are acquired.

Next, the control device 22 controls the scan driver 15 and the like, to reset each of the radiation detecting elements 7, with the binning number, the reset scan cycle and the on-time of the TFT 8 in the reset scan cycle at the time of the reset of the radiation detecting elements 7 before the image acquisition (that is, the binning number (2×1), the reset scan cycle Tr0 and the on-time Ton0 of the TFT 8 in the reset scan cycle at the time of the reset before the radiograph acquisition), which are previously set. Here, the reset is repeated to the same number as the number of resets executed in the radiograph acquiring process. Thereby, it is possible to enhance the stability of the image after the offset correction at a later stage.

Next, the control device 22 transitions to the charge accumulation mode of accumulating the charge in the radiation detecting elements 7 by applying the off-voltage to all the scan lines 5 through the scan driver 15, and waits for the previously set accumulation time for the first offset image (that is, the accumulation time Ti1 for the first image), in a state where the radiographic imaging apparatus 1 is not irradiated with the radiation, to perform the accumulation of the dark charge (first dark accumulation).

Next, the control device 22 transitions to the reading mode, and controls the scan driver 15, the reading circuit 17 and the like, to read the charge accumulated in each radiation detecting element 7, with the binning number, the reading scan cycle and the on-time of the TFT 8 in the reading scan cycle at the time of the first offset image acquisition (that is, the binning number (2×1), the reading scan cycle Tr1 and the on-time Ton1 of the TFT 8 in the reading scan cycle at the time of the first image acquisition), which are previously set, and acquire the image data of the first offset image (first dark reading).

Next, the control device 22 transitions to the charge accumulation mode again. The control device 22 applies the off-voltage to all the scan lines 5 through the scan driver 15, and waits for the previously set accumulation time for the second offset image (that is, the accumulation time Ti2 for the second image), in a state where the radiographic imaging apparatus 1 is not irradiated with the radiation, to perform the accumulation of the dark charge (second dark accumulation).

Next, the control device 22 transitions to the reading mode, and controls the scan driver 15, the reading circuit 17 and the like, to read the charge accumulated in each radiation detecting element 7, with the binning number, the reading scan cycle and the on-time of the TFT 8 in the reading scan cycle at the time of the second offset image acquisition (that is, the binning number (1×1), the reading scan cycle Tr2 and the on-time Ton2 of the TFT 8 in the reading scan cycle at the time of the second image acquisition), which are previously set, and acquire the image data of the second offset image (second dark reading).

By the above processes from the reset to the second dark reading process (offset image acquiring process), the first offset image and the second offset image are acquired.

After the offset image acquiring process, the control device 22 performs the lag (residual image) correction.

Figure 10A:
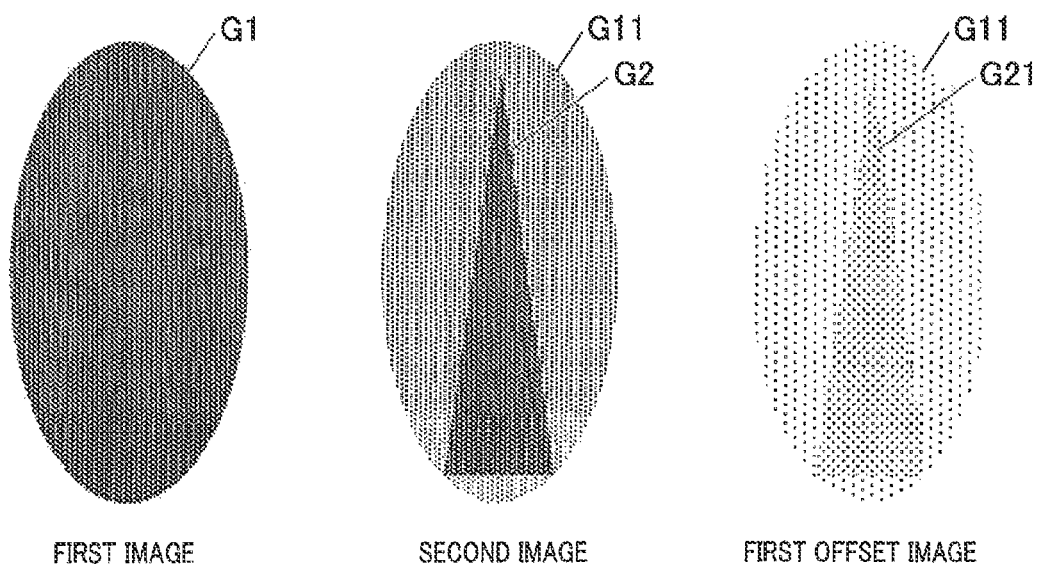
FIG. 10A is a diagram schematically showing a subject signal and lags in a first image, a second image and a first offset image in the second embodiment.
Figure 10B:
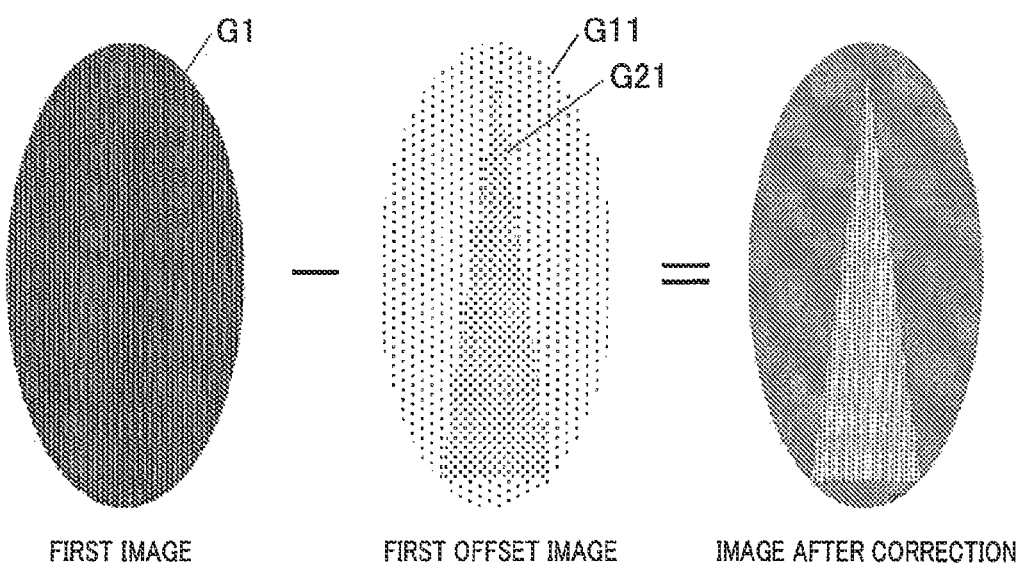
FIG. 10B is a diagram schematically showing the first image after a correction in which the first offset image is subtracted from the first image.

Here, as shown in FIG. 10A, in the case where the subject signal of the first image is G1, the second image is an image on which a lag G11 of the first image is superimposed in addition to a subject signal G2. On the first offset image, a lag G21 of the second image is further generated. Therefore, as shown in FIG. 10B, when the offset correction is performed by subtracting the first offset image from the first image with no change, an image in which the lag G21 of the second image appears as a virtual image is obtained. Hence, the lag correction for removing the virtual image is performed.

Figure 11:
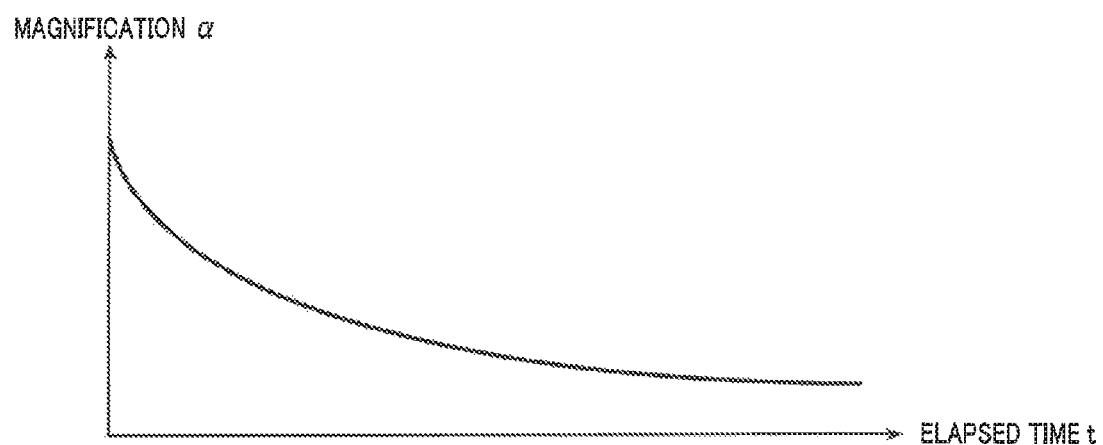
FIG. 11 is a graph showing a relation between an elapsed time t from a second image acquisition time point and a magnification a (a value indicating the ratio of a remaining lag to a lag in the second image) of a lag generated in an offset image in the case where a reset continues before an offset image acquisition.

FIG. 11 is a graph showing a relation between an elapsed time t from a second image acquisition time point and a magnification a (a value indicating the ratio of a remaining lag to a lag in the second image) of a lag generated in the offset image in the case where the reset continues before the offset image acquisition. As shown in FIG. 11, it is found that the lag to be generated in the offset image attenuates with elapse of time in the case where the reset continues before the offset image acquisition. The attenuation curve is evaluated by experiments. Hence, the control device 22 evaluates the magnification a, and performs the lag correction for the first offset image.

The magnification a can be calculated by the following method.

First, an image G in which the binning size of the second image is changed into the binning size of the first image is created. Here, an image G having a binning number of 2×1 is created by the digital binning of the second image. Next, a magnification a at which the average (or median) of the signal values of the image G is nearly equal to the average (or median) of the signal values of the first offset image is calculated. For example, the magnification a can be calculated by dividing the average of the signal values of the first offset image by the average of the signal values of the image G.

Then, from the signal value of each pixel of the first offset image, a value resulting from multiplying the signal value of the corresponding pixel of the image G by a is subtracted, and thereby, it is possible to remove the lag in the first offset image.

The lags G11, G21 sometimes exist in the second offset image. However, even when the lags G11, G21 remain in the second offset image, the lags G11, G21 do not appear as the virtual image in the second image after the offset correction process, and therefore, the lag correction may be skipped. Incidentally, the lag correction may be performed also for the second offset image. In this case, for example, a magnification 3 for the lag to be generated in the second offset image is calculated by dividing the average of the signal values of the second offset image by the average of the signal values of the second image. Then, from the signal value of each pixel of the second offset image, a value resulting from multiplying the signal value of the corresponding pixel of the second image by 3 is subtracted, and thereby, it is possible to remove the lag in the second offset image.

After the lag correction, the control device 22 performs correction processes such as the offset correction process, the gain correction process and the defective pixel correction process, and sends the image data of the corrected first image and second image to the console 58 through the communicator 39. The offset correction process is the same as the offset correction process described in the first embodiment, and therefore, the description is omitted.

When receiving the image data of the first image and the second image through the communicator 58c, the controller 58b of the console 58 generates the difference image between the first image and the second image, after equalizing the binning number between the first image and the second image by performing the enlargement interpolation process to the first image or performing the reduction interpolation (digital binning) process to the second image, and stores the first image, the second image and the difference image in the storage 59, in association with patient information, photographing condition and the like, or displays the first image, the second image and the difference image on the display device 58*a*.

Thus, in the second embodiment, similarly to the first embodiment, in the case of continuously photographing a plurality of radiographs (the first image and the second image) different in binning number, the radiographic imaging apparatus 1 acquires a plurality of offset images for the plurality of radiographs in which the binning number in resetting before the image acquisition and the binning number in acquiring the offset images are equal to those in resetting and acquiring the plurality of radiographs, and performs the offset correction process to the radiographs, respectively. Accordingly, it is possible to suppress the generation of the artifact in each of the radiographs due to the offset correction.

Furthermore, it is possible to perform a more accurate offset correction, by using the same accumulation time at the time of the acquisition of each of the plurality of offset images as the accumulation time at the time of the photographing of the corresponding radiograph.

Furthermore, it is possible to perform a more accurate offset correction, by acquiring a plurality of offset images respectively for the plurality of radiographs in which at least one of the reset scan cycle before the image acquisition, the on-time of the TFT 8 in the reset scan cycle, the reading scan cycle at the time of each image acquisition and the on-time of the TFT 8 in the reading scan cycle is equal to those at the time of the acquisition of the plurality of radiographs. Furthermore, by acquiring a plurality of offset images respectively for the plurality of radiographs in which all of the reset scan cycle before the image acquisition, the on-time of the TFT 8 in the reset scan cycle, the reading scan cycle at the time of each image acquisition and the on-time of the TFT 8 in the reading scan cycle are equal to those at the time of the acquisition of the plurality of radiographs, it is possible to nearly equalize the effective accumulation time (the total accumulation time from the completion of the last reset to the start of the reading after the accumulation of the charge) for each line of the scan lines 5 at the time of each offset image acquisition, with the effective accumulation time at the time of the corresponding radiograph acquisition, and therefore, it is possible to perform a more accurate offset correction.

Further, in the DES mode, by setting a greater number than 1 as the binning number in the longitudinal direction at the time of the acquisition of the first image that is photographed earlier, it is possible to perform a high-speed reading of the first image. Therefore, it is possible to shorten the photographing interval between the first image and the second image, and it is possible to suppress the artifact in the photographed image due to the body motion of the subject. Further, the first image photographed at a low tube voltage has a low graininess. However, it is possible to reduce the noise of the first image, by performing the reading of the charge accumulated by the photographing in which the subject is irradiated with the radiation at a low tube voltage (that is, the acquisition of the first image) at a greater binning number than that in the reading of the charge accumulated by the photographing in which the subject is irradiated with the radiation at a high tube voltage (that is, the acquisition of the second image).

The embodiment of the invention has been described above. The description in the above embodiment is a preferred example of the present invention, and the present invention is not limited to this.

For example, in the above first and second embodiments, it has been described that the first offset image and the second offset image are continuously acquired before or after the photographing of the first image and the second image, in response to one operation of the exposure switch 56, that is, the radiograph acquiring process and the offset image acquiring process are continuously performed. However, the offset image acquiring process may be performed in advance, and the first offset image and the second offset image may be acquired and stored in the storage 40. Then, after the acquisition of the first image and the second image, the first offset image and the second offset image may be read from the storage 40, and the offset correction process may be performed. Also in this case, the first offset image and second offset image acquired in one offset image acquisition process may be stored in the storage 40. Alternatively, average or median of first offset images and second offset images acquired in a plurality of offset image acquiring processes may be calculated, and may be stored in the storage 40 as the first offset image and the second offset image, respectively. By evaluating the average or median of a plurality of offset images, it is possible to reduce offset noise. Further, the plurality of offset images acquired in the plurality of offset image acquiring processes may be stored in the storage 40, in association with the acquisition time or acquisition order, and in the case where an offset difference is generated due to a difference in the acquisition time of the offset image, the average may be evaluated after a heavy weight is given to an image with a late acquisition time and a light weight is given to an old image. Thereby, it is possible to achieve both the coincidence of the offset and the reduction in offset noise.

Further, in the above embodiments, the radiographic imaging apparatus 1 performs the offset correction process, and then sends the image data to the console 58. However, the radiographic imaging apparatus 1 may send a set of a plurality of radiographs before the offset correction and a plurality of offset images, to the console 58, and the controller 58*b* of the console 58 may perform the offset correction process to each of the plurality of radiographs, using the offset images respectively for the plurality of radiographs received from the radiographic imaging apparatus 1 through the communicator 58*c*. That is, all processes from the acquisition of the radiographs and the offset images to the offset correction process may be completed by the radiographic imaging apparatus 1, or may be completed by the system including the radiographic imaging apparatus 1 and the console 58.

In addition, the detailed configurations and detailed operations of the apparatuses that constitute the radiographic imaging system can be modified when appropriate, without departing from the spirit of the present invention.

Although embodiments of the present invention have been described and illustrated in detail, the disclosed embodiments are made for purposes of illustration and example only and not limitation. The scope of the present invention should be interpreted by terms of the appended claims.

The description, claims, drawings and abstract of Japanese Patent Application No. 2018-162273 filed to Japan Patent Office on Aug. 31, 2018 are incorporated herein by reference in its entirety.

What is claimed is:

1. A radiographic imaging system comprising:
a plurality of radiation detecting elements that is two-dimensionally arrayed; and
an image acquiring circuit that acquires an image by causing the plurality of radiation detecting elements to accumulate and release charges and by reading the released charges, the charges being released during resetting of the plurality of radiation detecting elements;
and a hardware processor that performs:
a radiograph acquiring process of controlling the image acquiring circuit to successively acquire a plurality of radiographs while changing at least a binning number;
an offset image acquiring process of controlling the image acquiring circuit to acquire a plurality of offset images respectively for the plurality of radiographs in which a binning number in resetting the plurality of radiation detecting elements before acquiring the plurality of offset images and binning numbers in acquiring the plurality of offset images are equal respectively to a binning number in resetting the plurality of radiation detecting elements before acquiring the plurality of radiographs and binning numbers in acquiring the plurality of radiographs; and
an offset correction process of performing an offset correction on the plurality of radiographs by using the plurality of offset images respectively for the plurality of radiographs,
wherein the plurality of offset images includes a first offset image and a second offset image, and the plurality of radiographs includes a first radiograph and a second radiograph,
a binning number in resetting the plurality of radiation detecting elements before acquiring the first offset image is equal to a binning number in resetting the plurality of radiation detecting elements before acquiring the first radiograph,
a binning number of the first offset image is equal to a binning number of the first radiograph, and
a binning number of the second offset image is equal to a binning number of the second radiograph.

2. The radiographic imaging system according to claim 1, wherein in the offset image acquiring process, the hardware processor acquires the plurality of offset images respectively for the plurality of radiographs in which charge accumulation times of the plurality of radiation detecting elements in acquiring the plurality of offset images are equal respectively to charge accumulation times of the plurality of radiation detecting elements in acquiring the plurality of radiographs.

3. The radiographic imaging system according to claim 1, wherein
the image acquiring circuit includes a switch that causes the plurality of radiation detecting elements to release the charge in response to being turned into an on-state, and
in the offset image acquiring process, the hardware processor acquires the plurality of offset images respectively for the plurality of radiographs in which at least one of a reset scan cycle, an on-time of the switch in the reset scan cycle, a reading scan cycle, and an on-time of the switch in the reading scan cycle in acquiring the plurality of offset images is equal respectively to a reset scan cycle, an on-time of the switch in the reset scan cycle, a reading scan cycle, and an on-time of the switch in the reading scan cycle in acquiring the plurality of radiographs.

4. The radiographic imaging system according to claim 1, further comprising: a radiation irradiating apparatus that irradiates the plurality of radiation detecting elements with radiation at different tube voltages multiple times, wherein
in the radiograph acquiring process, the hardware processor acquires the plurality of radiographs corresponding to the radiation at the different tube voltages.

5. The radiographic imaging system according to claim 4, wherein in the radiograph acquiring process, the hardware processor controls the image acquiring circuit to read a radiograph taken with a radiation at a low tube voltage at a greater binning number than a radiograph taken with a radiation at a high tube voltage.

* * * * *